United States Patent
Laughlin et al.

(10) Patent No.: US 10,627,321 B2
(45) Date of Patent: Apr. 21, 2020

(54) AIR SAMPLER

(71) Applicants: Robert Laughlin, Miramar, FL (US); Katrin Laughlin, Miramar, FL (US)

(72) Inventors: Robert Laughlin, Miramar, FL (US); Katrin Laughlin, Miramar, FL (US)

( * ) Notice: Subject to any disclaimer, the term of this patent is extended or adjusted under 35 U.S.C. 154(b) by 0 days.

(21) Appl. No.: 16/132,369

(22) Filed: Sep. 15, 2018

(65) Prior Publication Data

US 2020/0088610 A1    Mar. 19, 2020

(51) Int. Cl.
 *G01N 1/22* (2006.01)
 *C12M 1/22* (2006.01)

(52) U.S. Cl.
 CPC ........... *G01N 1/2205* (2013.01); *C12M 23/10* (2013.01); *G01N 1/2226* (2013.01); *G01N 1/2273* (2013.01); *G01N 2001/2238* (2013.01)

(58) Field of Classification Search
 CPC .. G01N 1/2205; G01N 1/2226; G01N 1/2273; C12M 23/10
 See application file for complete search history.

(56) References Cited

U.S. PATENT DOCUMENTS

| | | | | |
|---|---|---|---|---|
| 5,206,818 A | * | 4/1993 | Speranza | G01M 3/205 702/24 |
| 5,437,199 A | * | 8/1995 | Kaplan | B63C 11/18 73/863.23 |
| 2010/0330603 A1 | * | 12/2010 | Zhu | C12Q 1/02 435/29 |
| 2012/0152038 A1 | * | 6/2012 | Cho | G01N 1/2205 73/863.12 |

* cited by examiner

*Primary Examiner* — David Z Huang
(74) *Attorney, Agent, or Firm* — Christopher J. Vandam, PA; Chris Van Dam

(57) ABSTRACT

An air sampler that receives an air source through a manifold. The manifold has a restrictor and a vent that opens above a specified pressure. The remaining portion of the air source enters the inlet assembly where it passes through a filter with a removable element then through a one way valve and into an impermeable bag. Excess air in the bag escapes out an outlet one way valve capturing a sample inside the bag. An ambient air sample may delivered via a hand squeeze bulb and a biological sample may be contained inside the bag.

4 Claims, 4 Drawing Sheets

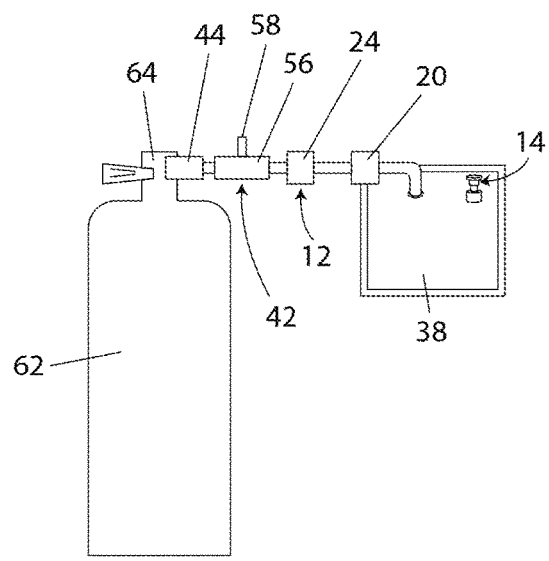
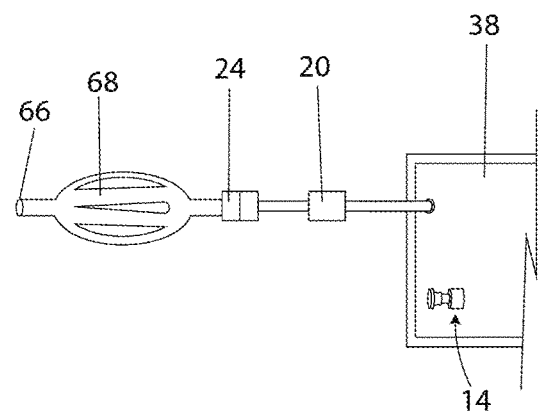
FIG. 3
FIG. 4
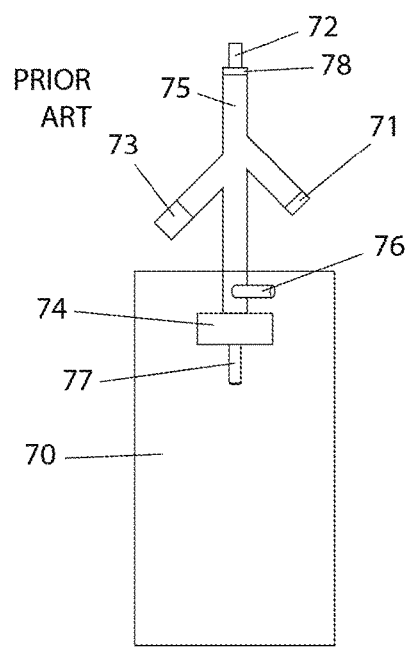
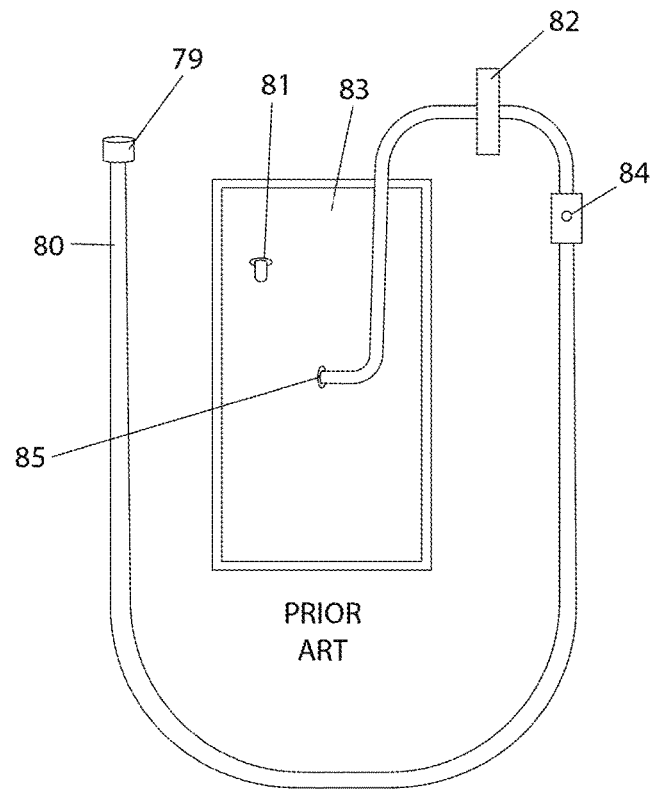
FIG. 5
FIG. 6

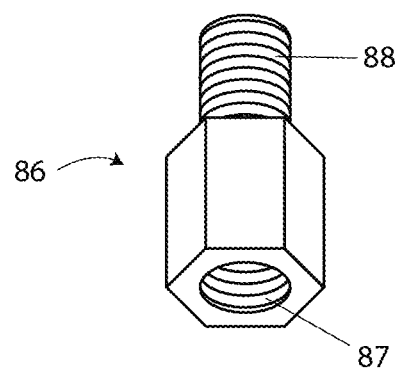
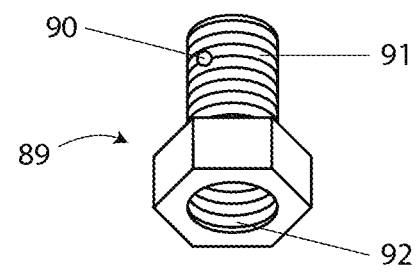
FIG. 7       FIG. 8
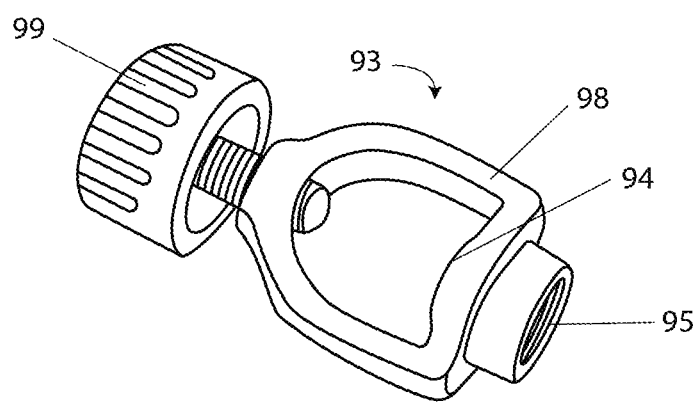
FIG. 9

AIR SAMPLER

BACKGROUND OF THE INVENTION

1. Field of the Invention

The present invention relates to testing of breathable gases, and more particularly, to an improved device and process to collect a sample of gas from a pressurized source or ambient air.

2. Description of the Related Art

Several designs for gas collection devices have been designed in the past. None of them, however, includes a compact system adapted for transport by common carrier by having a low pressure sample reliably contained in a non-explodable safety bag that is filled from very high pressure sources to near ambient pressure sources that further includes a filter with a measurable element and optionally a biologic sample collector inside the bag.

Applicant believes that the closest reference corresponds to U.S. Pat. No. 5,437,199 issued to Kaplan. The Kaplan device is demonstrated in FIG. 6 and comprises a connector 79, a tube 80, a relief valve 81, a filter 82, a bag 83, a vent 84 and a nipple 85.

The Kaplan device differs from the present invention because, among other reasons, the present device and method provide for a filter that has a removable element for quantitative and qualitative analysis that captures its sample a short distance from the air source and where the filter remains outside of the contained air sample. Further, the present design includes a one way valve where the collected gas enters the bag which leaves the filter, fittings and tubes apart from the sample during the time between collecting the sample and analysis of the sample. Also, the present design has a controlled pressure vent before the filter that regulates the maximum pressure that the bag and filter are exposed to during obtaining a high pressure gas sample.

Kaplan shows and describes the device in FIG. 6 where the connector 79 connects to a high pressure source, such as an air tank. The sampled gas then travels down tube 80 under high pressure. In the tube 80 any contaminants in the sample could adhere to the inside of the tube 80 where it could not be measured or tested. The sample continued to the vent 84 where at least part of the sample freely escapes and is open to the ambient air.

This design is problematic in that a sample injected into the bag 83 can freely exchange with the outside air through the vent 84. The relief valve 81 is merely for over-pressure relief. Although unclear from Kaplan the connector 79 may also be open for gas exchange between the time of taking the sample and when it could be examined.

The filter 82 in Kaplan also has no provision for measuring or analyzing any particulate or other material captured by the filter 82. The filter 82 itself should be analyzed for impurities which is solved by the present disclosure. Further, the sample in the bag 83 is able to move both directions past the filter 82 in transport because the filter 82 is not removed from being in communication from the sample in the bag during the hours or days in transport to the testing facility. This is evidenced by the nipple 85 is not a one way valve in Kaplan's device.

Other prior art, as exemplified in FIG. 5, comprises a vessel 70, a burst disc 71, an inlet 72, a valve 73, a filter 74, a manifold 75, a vent 76, an outlet 77 and a restrictor 78. A primary problem with this design is the use of a high pressure metal cylinder that can easily be over-pressurized. The burst disk 71 only protects against extreme high pressure events. This design cannot work with low pressure samples.

The restrictor 78 limits the rate at which a sample is taken but not the pressure. The vent 76 into the vessel 70 avoids some sampled air to avoid the filter 74. The filter 74 also does not open to allow examination and measurement of a filter element which can provide important information to the gas analysis. Further yet, the filter 74 remains in the pressurized vessel 70 during transport to the analysis facility that can affect the gas sample.

These types of containers also use imprecise burst discs 71 and valves 73 that also contribute to the risk of bursting and compliance with shipping regulations for over-pressurized gases. Further, by using a metal cylinder and collection manifold the cost of the device is greatly increased and more potential for end users altering the device greatly decreases the safety of the device.

Other patents describing the closest subject matter provide for a number of more or less complicated features that fail to solve the problem in an efficient and economical way. None of these patents suggest the novel features of the present invention.

A brief abstract of the technical disclosure in the specification and title are provided as well for the purposes of complying with 37 CFR 1.72 and are not intended to be used for interpreting or limiting the scope of the claims.

Without limiting the scope of the invention, a brief summary of some of the claimed embodiments of the invention is set forth below. Additional details of the summarized embodiments of the invention and/or additional embodiments of the invention may be found in the detailed description of the invention below.

SUMMARY OF THE INVENTION

It is one of the main objects of the present invention to provide an easy to use air sampling device and method of use.

It is another object of this invention to provide an air sampling device and method of use that is safer to use and transport without risk of explosive bursting.

It is still another object of the present invention to provide an air sampling device and method of use that has a filter positioned to best collect particulate matter and that is readily testable without contamination of the sample between obtaining the sample and testing the sample.

Another object of the present invention is to provide an air sampling device and method of use that works with a variety of high and low pressure sources efficiently and safely.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

These and other embodiments which characterize the invention are pointed out with particularity in the claims annexed hereto and forming a part hereof. However, for a better understanding of the invention, its advantages and objectives obtained by its use, reference can be made to the drawings which form a further part hereof and the accompanying descriptive matter, in which there are illustrated and described various embodiments of the invention.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 3 shows an elevation view of an air sampler during the process of obtaining a sample.

FIG. 4 shows a partial elevation view of a sampler during the process of obtaining a sample from ambient air.

FIG. 5 shows an elevation cross section of an example from the prior art.

FIG. 6 shows an elevation view of another example from the prior art.

FIG. 7 shows a perspective view of an example of an adapter.

FIG. 8 shows a perspective view of an example of an adapter.

FIG. 9 shows a perspective view of an example of an adapter.

DETAILED DESCRIPTION OF THE PREFERRED EMBODIMENT

Figure 1:
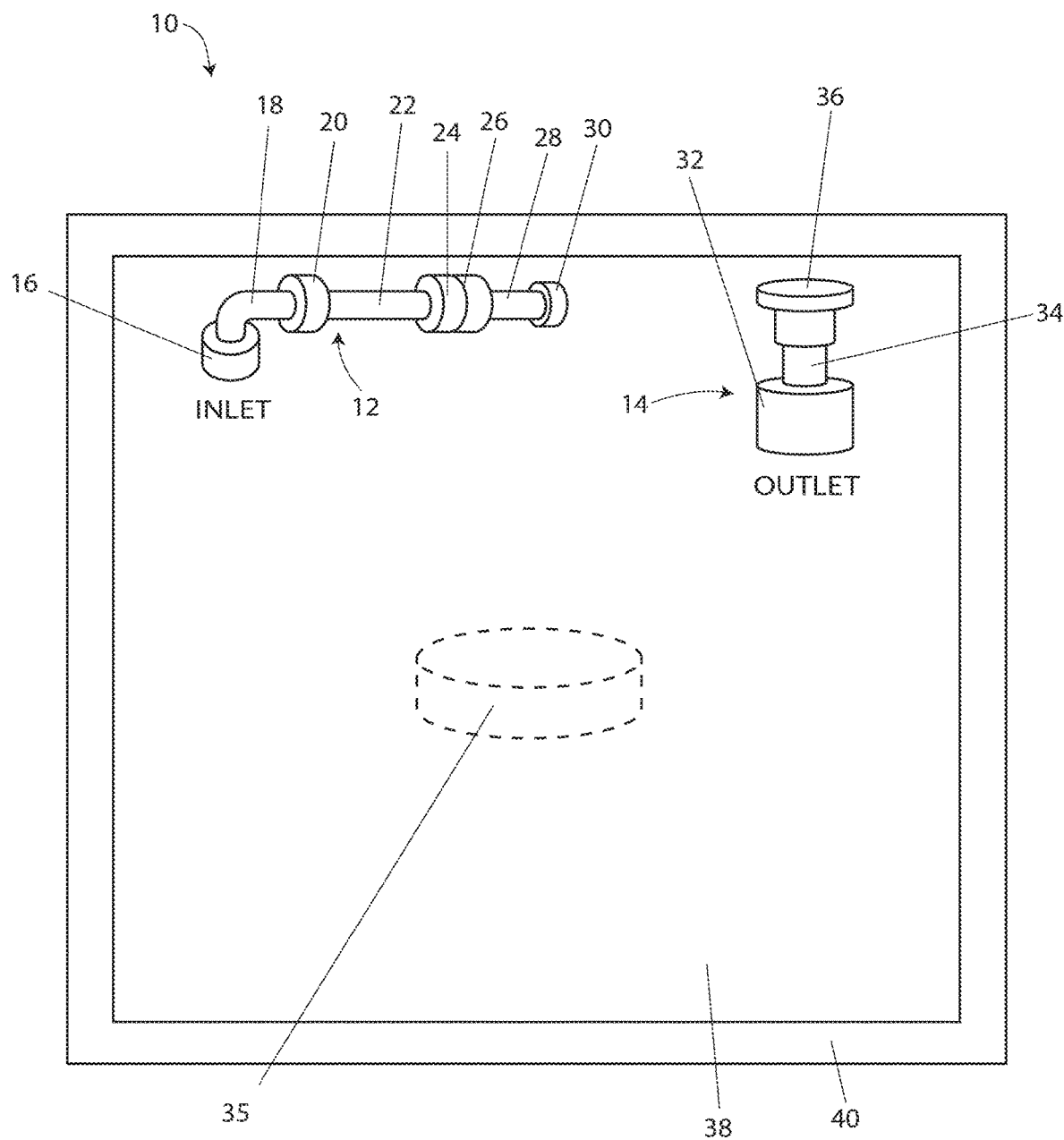
FIG. 1 shows a perspective view of an air sampling device as may be configured prior to use or ready for to transport.

While this invention may be embodied in many different forms, there are described in detail herein specific embodiments of the invention. This description is an exemplary of the principles of the invention and is not intended to limit the invention to the particular embodiments illustrated and described.

For the purpose of this disclosure, like reference numerals in the figures shall refer to like features unless otherwise indicated or is obvious by context.

The subject device and method of use is sometimes referred to as the device, the invention, the bag, the sampler, the air sampler, the machine, the system, the process or other similar terms as apparent from the context. These terms may be used interchangeably as context requires and from use the intent becomes apparent. The masculine can sometimes refer to the feminine and neuter and vice versa. The plural may include the singular and singular the plural as appropriate from a fair and reasonable interpretation in the situation.

Referring now to the drawings, where the present invention is generally referred to with numeral 10, it can be observed that it basically includes an inlet assembly 12, an outlet assembly 14, a nipple 16, an elbow 18, a valve 20, a tube 22, a filter 24, a seam 26, a connector 28, a cap 30, a nipple 32, a valve 34, a collector 35, a cap 36, a bag 38, a margin 40, a manifold assembly 42, an adapter 44, a gasket 46, an aperture 48, an aperture 52, an o-ring 54, a manifold 56, a valve 58, a connector 60, a tank 62, a neck 64, an inlet 66 and a bulb 68.

Looking at FIG. 1, the bag 38 is generally constructed of a flexible and impermeable material forming a front and a back panel with a hollow interior. The front and back panels are unified together around a margin 40 forming a hermetic seal to keep a sample of gas inside the bag 38.

The inlet assembly 12 is affixed to the bag 38 at the nipple 16. The nipple 16 traverses the front panel of the bag 38 and is completely airtight with the bag 38. The elbow 18 may be present and is connected to the nipple 16 to direct the flow of the sampled gas into the bag 38. The elbow 18 may be rigid or flexible tubing and helps the inlet assembly 12 lay flat against the bag 38 for more compact shipping.

Near the nipple 16 is a one way valve 20 that allows the sample to pass through into the bag 38 but preventing any venting through the inlet assembly 12. Having the valve 20 near the bag 38 and closer to the nipple 16 than the filter 24 keeps the air sample nearly entirely inside the bag 38 with very little of the sample remaining in the elbow 18 (or substitute tube) between the nipple 16 and the valve 20.

Any handling or jostling the bag 38 after the sample is taken will not allow the sample to back-flow over the filter 24. In other words, not only does the valve 20 keep the sample in the bag 38, it also prevents any reverse air flow through the filter that could dislodge any particulate that was caught in the filter. This enhances the detection ability of the filter and increases confidence that particulate has been captured for measurement and analysis.

The filter 24 may include a particulate filter element that the air sample passes through when pushing into the bag 38. The filter element captures a predetermined size and class of particulate matter that is carried with the incoming air sample. For example, a filter may be adapted to capture a particular particle size, ionic charge, type of particulate or other characteristic.

It should be appreciated that the terms particulate, contaminants, oils and similar terms collectively refer to any component of the air being sampled that is other than a pure sample of the prescribed gas. For example, these can comprise oils, solid particles, waxes, rust, grime, dirt, dust, foams, cleaners, metals, ash, chemical compounds, soot, dander, molds, bacteria, biologicals, pesticides, organic compounds, pollen, toxins, solvents or any other recognized impurity in the gas from which the sample is collected.

A filter element may be, for example designed to capture aerosolized oils and/or particulates in the 0.02 (two hundredths) micron or larger range in some testing parameters. The nature of the filter should be selected to be compatible with the anticipated air flow volume and pressure in light of the anticipated particulate constituents to ensure sufficient sample acquisition rates and suitability for the particulate. A filter element should allow enough flow to both effectively accept a sample of air and also be effective at trapping the anticipated particulate.

The housing of the filter 24 should preferably be openable at a seam 26 to be able to open the filter and remove the filter element for analysis. The filter element may be weighed and compared to a standard for quantitative analysis. This may be used in a calculation along with the time over which the sample was collected to extrapolate a value for particulate content of the sample.

The seam 26 may include a tamper-evident frangible seal to indicate whether the filter 24 has been opened or previously used and must be discarded to ensure an authentic sample of the gas sample presently collected.

The filter element may also be chemically analyzed for the specific content of the particulate captured on the filter element. For example, Fourier transform infrared spectroscopy (FTIR) has been shown to be effective in determining the constituent content of the captured filter particles and also of the air sample itself.

Other methods of analysis of the filter and the air sample could develop over time and are not critical to design of the present air sample. For example, isotope ratio mass spectrometry (IRMS) may be available and preferred for some testing of anticipated contaminants or adapted to the specific makeup of the filter element. However, IRMS may have some cost and complexity disadvantage for some applications. Similarly, non-dispersive infrared spectroscopy (NDIRS) may be attractive for other means of quantitative analysis of the both the air sample and the filter element after collecting the air sample.

The location of the filter 24 is the first substantive element that the newly collected air sample encounters after a short connector 28. This helps ensure that any particulate or other contaminants are first captured by the filter 24 instead of sticking to or otherwise collecting in valves, tubing or other elements of the inlet assembly 12.

A cap 30 is provided to seal the source end of the inlet assembly 12 both prior to collection of the gas sample and after the sample is collected for transport to the testing facility. The cap 30 may be friction fit or threaded. There is essentially no back pressure on the cap 30 because the valve 20 prevents reverse flow of any of the sample gas backwards out of the inlet assembly.

The outlet assembly 14 is also affixed to the bag 38 at a nipple 32. The nipple 32 transitions from the interior of the bag 38 to the one way valve 34. The valve 34 is calibrated to vent the bag 38 at a predetermined internal pressure of the sample gas inside the bag 38. The pressure that opens the one way valve 34 determines the total maximum pressure experienced inside the bag.

An effective example of the relief pressure of this valve 34 may be about one PSI. However, this could range depending on the capability of the bag 38 itself and other criteria determined by the nature of the gas sample desired. The range of commonly sampled gases would allow for a relief valve 34 capacity of anywhere from about 0.1 PSI to about fifteen PSI, but could be higher for certain applications and for specific gases sampled by the air sampler.

The valve 34 prevents any over-pressure of the bag 38. This effectively means that the bag 38 cannot burst. This has significance in that different modes of transport can be safely made with this design. For example, in an unpressurized cargo aircraft if the pressure differential in the cargo hold is such that the inside pressure exceeds this differential the bag 38 will preserve the integrity of both the bag 38 and the air sample contained inside.

By using valve 20 and valve 34 together the filling of the bag 38 is essentially automatic controlled. When any pressure of gas is introduced into the manifold assembly 42 the volume and pressure of the gas is initially moderated by the aperture 52 and the valve 58. The gas ultimately introduced into the bag 38 has some overflow out of valve 34 to flush the elements of the air sampler and particularly the bag 38, typically several minutes. When the air source is terminated the sample is automatically captured between valve 34 and valve 20 inside the bag 38. Adding caps 36 and 30 further seal inside the air sample.

A cap 36 may be provided to prevent the intrusion of contaminants into the valve 34 and bag 38 prior to acquisition of the gas sample and during transport of the sample to the testing facility. Similar to the cap 30 on the inlet assembly 12 the cap 36 on the outlet assembly 14 may have a frangible seal to provide evidence of tampering prior to collection of a gas sample. The filter 24 may also include a frangible seal as well to provide evidence of tampering.

The interior of the bag 38 may also contain a biological collector 35. This may take the form of a petri-style dish with an agar medium to capture and foster bio-material from the gas sample. Other types of culture containment devices and culture mediums may be used as required by the nature of the anticipated sample. For example, spores, molds, bacteria and viruses could be adapted to be made from a particular medium to harbor that organism until the time that testing could be made. Other collection containers like a perforated spheroid or other three dimensional structure for the growth medium could also be effectively used to protect the sample until testing occurs.

When the air sampler is being prepared for laboratory testing the gas sample may be removed from the outlet assembly 14, then through the valve 34 thereby avoiding contamination of the sample. The gas sample could also be removed through the outlet assembly 14 into the testing apparatus. Once the gas sample is tested the bag may be opened to access the collector 35 for concentrated analysis of the collector 35. This preserves both the integrity of the gas sample and the biological medium sample.

Figure 2:
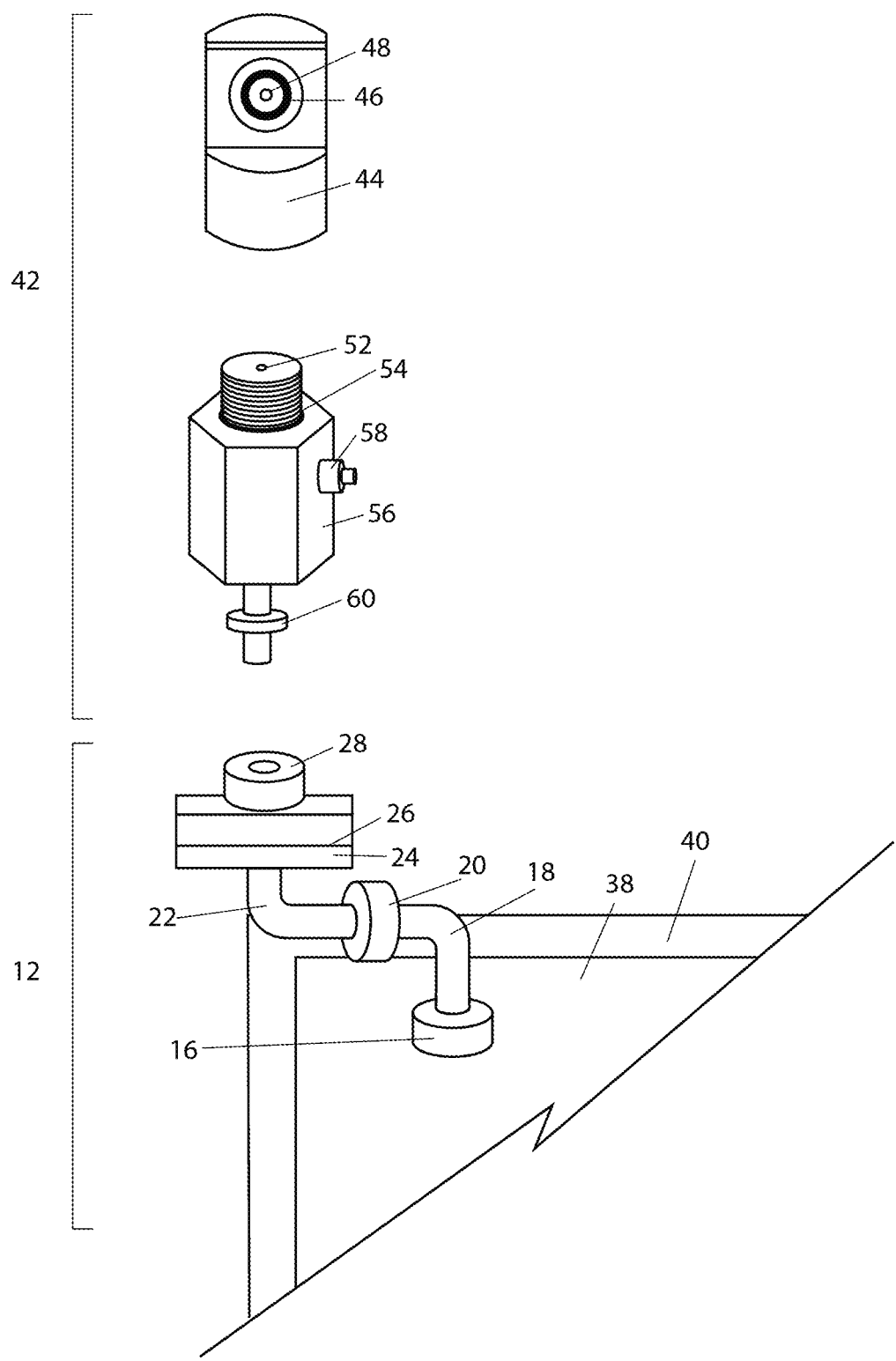
FIG. 2 shows an exploded perspective view of the elements of a manifold assembly and an inlet assembly as may be configured for taking a sample of gas.

FIGS. 2 and 3 in combination show an example of the air sample device configured for operation to collect a sample. In addition to the inlet assembly 12 as described above that remains attached to the bag 38, there is a manifold assembly 42 needed to complete the connection to a pressurized air source, such as a tank 62. The manifold assembly 42 generally comprises an adapter 44 and a manifold 56. Each of these are preferably made of metal to ensure durability for many uses of the manifold assembly 42 for successive air samples using new bags 38 each time a sample is taken.

The adapter 44 that is configured for the specific fitting on the tank 62. For example, tanks generally suited for fire fighting have a style of fitting that is different from several types of connectors used on SCUBA equipment. Other types of gas cylinders have varying types of connectors on the tank. A manifold assembly 42 kit may be provided that has adapters 44 design to connect to a preselected set of pressurized tanks that the user desires to test. There are many styles and configurations of tank fittings commonly used across a wide variety of industries and for specific applications.

The adapter show in FIGS. 2 and 3 is generally suited for a SCUBA type tank 62. The gasket 46 is set around the gas receiving aperture 48. The aperture 48 generally aligns with a mating aperture in the neck 64 of the tank 62. The gasket 46 provides an airtight seal against the valve in the neck 64 of the tank 62. There may be a yoke or other necessary means to physically secure the adapter 44 to the top of the tank 62 so that the tank 62 is in gaseous communication with the aperture 48 so that the gas sample may be delivered through a passageway inside the adapter 44 through the aperture 52 that completely traverses through the manifold 56.

The aperture 52 may be threaded on the interior and able to accept a threaded set screw or similar hardware that itself has an aperture through it. Alternate screws may have differing diameters to increase or decrease the rate at which gas can be delivered to the bag 38. If present, this set screw may be replaced in the field by the technician taking the sample of gas. Alternatively, multiple different manifold fittings with a fixed size aperture 52 may be supplied with the manifold kit.

The exact dimension of the aperture 52 is dependent on the pressure and the nature of the gas being sampled. For most gas samples and pressures an aperture of about a ten thousandth to several ten thousandths of an inch may be usable. Larger or smaller apertures 52 remain within the scope of the inventive concept of this air sampler.

A manifold 56 is provided to connect any of the available adapters 44 needed for the specific tanks 62 to the manifold 56 that is used with pressurized sources of gas. There may be one or more adapters 44 in a kit that can be used with the manifold 56. On one end of the adapter 44 should be able to fit into the upstream side of the manifold 56 and should seat against the o-ring 54. The threaded manifold should generally seal airtight with mere hand tightened pressure against the o-ring 54. The manifold 56 may also include a similar o-ring 54 to seal the manifold 56 against the adapter 44. A wrench fitting may also be provided on the exterior of each the adapter 44 and the manifold 56 to afford more purchase to each of these elements to ensure strong and airtight connections.

FIGS. 7, 8 and 9 show examples of alternative adapter assemblies 86, 89 and 93, respectively. These adapter assemblies 86, 89 and 93 may be suited for use with specific different styles of tanks or other sources of air to be sampled. The adapters 86, 89 and 93 have threads 87, 92 and 95, respectively, to connect to a manifold 56 that guides the sample into the bag 38.

Depending in the nature of the connection means to the source of the air to be sampled there may be uninterrupted threads 88, as seen in FIG. 7. In others, as seen in FIG. 8 there may be an aperture 90 to guide the flow of gas to the manifold through the interior of the adapter assembly. An airtight seal between the adapter assembly and the manifold assembly is preferred to ensure integrity of the sample.

The example of adapter shown in FIG. 9 is particularly configured for use sampling a yoke-style SCUBA tank. This may be used to test the contents of a SCUBA tank that has been associated with an injury to verify the contents of that cylinder. Of course other configurations of adapters may be best used with other types of connections to tanks and sources within the inventive scope.

It should be appreciated that although the term tank is used in this description and that gases are often stored in tanks that any pressurized gas source may be used to supply the sample of gas to be tested by the present device. For example, compressors, reaction vessels, vents and other sources are each suitable to provide a gas sample that is compatible with this system.

The manifold 56 has a connector 60 that is connected to the connector 28 on the inlet assembly 12. This connection may be threaded, friction fit or other type of connecting style. There may be a gasket or o-ring in the interface between the connector 60 and connector 28 to ensure an airtight and leak-free connection.

The manifold 56 has an aperture 52 through it to allow passage of the sampled gas. The aperture 52 is dimensioned to limit the rate that the gas sample enters the bag 38. Essentially, the aperture 52 is a simple restrictor to prevent damage to the components of the air sampler that could be caused by high pressure sample sources. This design allows essentially unlimited pressure from the gas being sampled without substantial risk to the user of components of the device. The restrictor aperture 52 may alternatively be located in the adapter 44 or in the upstream side of the manifold with similar performance results.

The manifold 56 also includes a valve 58 that limits the pressure of the gas sample delivered to the bag 38. The valve 58 is a one way relief valve with a precise pressure setting at which it exhausts excess gas and thereby reduces the pressure passed through the manifold 56. It is preferred that the valve 58 sensitivity is high enough to ensure that a complete sample of gas is passed through the manifold 56 without excessive dumping out the valve 58 and also low enough to not over pressure the bag 38 which could cause the bag to fail and loss of the sample.

For at least one combination of materials of the bag 38 and typical pressures of breathing gases being sampled a relief pressure of the valve 58 could be approximately two tenths pounds per square inch (psi). Relief values of between about one tenth of one psi and fifteen psi for the valve 58 will be appropriate for the majority of applications. However, the nature of the gas being sampled, the pressure at which the gas is delivered, the desired pressure of the sample and the materials of the component parts that are easily calculated.

FIG. 4 shows a version of the air sampler that includes a similar bag 38, outlet assembly 14, valve 20 and filter 24 as described in the other variations of the device described herein. A difference is the use of a bulb 68 with an inlet 66. This style of device does not need an external pressurized source of gas.

A one way valve 20 is included on the inlet side of the device. This allows gas to be pumped into the bag 38 but not back fed into the bulb 68 from the bag 38. A one way valve is included in the outlet assembly 14 to provide relief in the event of over-pressuring. The outlet assembly 14 has a relief pressure of about 0.2 PSI for most applications, but can vary between about a tenth of one PSI to about fifteen PSI depending on the nature of the bulb 68 and the bag 38.

The bulb 68 is flexible and is hand squeezed to expel air through the filter 24 and into the bag 38. The bulb 68 is then released and new air is draw into the bulb through the inlet 66. In this way unpressurized air, for example in a room, can be sampled easily without equipment other than that shown in FIG. 4.

Room air or other particular samples can readily be taken with the device in FIG. 4. For example, air can be drawn into the inlet 66 from an air conditioning or heating vent to determined the air quality being pushed into a living or work area. By way of another example, outdoor air can be sampled for pollutants, pollen, smoke or a wide variety of other thing in the environment.

In one example of how an air sampler could be made and used the bag is made of an impermeable plastic sheet such as polyester having an interior volume of about three hundred milliliters. This volume could range substantially smaller or larger as determined by the testing requirements of the laboratory. The size of the bag is not determination of the inventive concept. For example, the bags could be from a couple milliliters to several liters.

The tank being sampled may typically be a fireman's self contained breathing apparatus or a diver's self contained underwater breathing apparatus. In practice, the air mixtures in these must generally be tested for regulation compliance periodically. By providing a kit of the reusable parts comprised of the manifold assembly the overall cost for testing air samples is limited to the cost of bag with associated inlet and outlet assemblies as generally shown in FIG. 1.

The manifold kit may include several adapters for different fittings on various styles of air tank or other air sourced to be sampled. The manifold kits are generally retained by the entity taking the samples. The manifold kits are separated from the bag assemblies and only the bag assemblies are sent into the lab for testing.

An important version of the invention can be fairly described as an air sampler comprised of a bag, an inlet assembly, a one way outlet valve and a manifold assembly. The term air is intended to mean any gas. The bag is air-impermeable with an interior volume and generally sealed around the edges. The manifold assembly is connected to an air source to be sampled, such as a high pressure source or from ambient air. The manifold assembly remains outside of the bag and can be reused when sampling air into other bags. The manifold assembly includes an aperture to restrict the volume of air passing through the manifold assembly from the air source to prevent over-pressure of the components. Downstream of the aperture is a one way relief valve that vents overboard into the air a portion of the air source over a preselected pressure. An un-vented portion remaining of the air source that did not exit the one way relief valve exits the manifold and into the inlet assembly then through a filter, then through a one way inlet valve keeping the air into the bag and then into the bag through an airtight seal with the bag. The inlet assembly may be entirely inside or outside of the bag. The manifold remains outside the bag and is separable from the inlet assembly so that the inlet assembly stays with the bag but the manifold assembly may be separated from the bag and inlet assembly and removed. The bag collects the un-vented air source in the interior volume until it is full. The one way outlet valve is connected to the bag through an airtight seal to keep a sample in the bag. The un-vented air in excess of a capacity of the interior volume of the bag is vented out of the bag through the one way outlet valve. The air source generally flushes through the vents and bag to get a representative sample of air and then the air source is stopped and the sample is automatically captured in the bag. The bag with sample sent to a lab for analysis, with or without the manifold assembly. Optionally, a biological collector, such as a petri dish with agar is sealed inside the bag. Optionally, the filter opens and contains a removable filter element that is tested outside the filter housing. Optionally, the air source is a pressurized cylinder, tank or pump. Optionally, the air source is a hand squeezed bulb connected to the inlet assembly that moves ambient air into the bag without use of a manifold assembly.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An air sampler comprised of a bag, an inlet assembly, a one-way outlet valve and a manifold assembly; wherein the bag is air-impermeable with an interior volume;

the manifold assembly includes an adapter specific to an air source to be sampled;

the manifold assembly consists essentially of two elements; wherein the two elements are a manifold and the adapter; the manifold assembly adapter is directly connected to the air source to be sampled;

the manifold assembly adapter includes a gas receiving aperture which restricts the volume of air passing through the manifold assembly from the air source to be sampled;

downstream of the gas receiving aperture, within the manifold of the manifold assembly, a manifold aperture receives the air from the adapter, wherein the manifold aperture is surrounded by the adapter, and a one way relief valve that vents a portion of the air source over a preselected pressure between 0.1 psi to 15 psi to limit the pressure of the air source passing to the inlet assembly and reduce pressure through the manifold of the manifold assembly and the inlet into the bag;

an un-vented portion of the air source exits the manifold of the manifold assembly and into the inlet assembly then through a filter, then through a one-way inlet valve and then into the bag through a first airtight seal with the bag;

the bag collects the un-vented portion of the air source in the interior volume;

the inlet assembly, comprised of the filter and the one-way inlet valve, remains affixed to the bag before, during and after collection of the sample;

the one-way outlet valve is connected to the bag through a second airtight seal; and the un-vented portion of the air source in excess of a capacity of the interior volume is vented out of the bag through the one-way outlet valve.

2. The air sampler in claim 1 further characterized in that a non-filtering biological collector comprised of an agar plate is sealed inside the bag.

3. The air sampler in claim 1 further characterized in that the filter contains a removable filter element that captures oil and particulate in the air source as it passes through the filter element and the filter opens to remove the filter element from the filter after the sample is collected for analysis of any oil or particulate captured on the filter element.

4. An air sampler as in claim 1 further characterized in that the air source is a pressurized cylinder, tank or pump.

* * * * *